(12) United States Patent
Puckett, Jr. et al.

(10) Patent No.: US 10,039,658 B2
(45) Date of Patent: Aug. 7, 2018

(54) EXPANDING SHEATH TIP

(71) Applicant: Cook Medical Technologies LLC, Bloomington, IN (US)

(72) Inventors: Dean R Puckett, Jr., Bloomington, IN (US); Brent A Mayle, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 222 days.

(21) Appl. No.: 14/885,229

(22) Filed: Oct. 16, 2015

(65) Prior Publication Data

US 2016/0106562 A1 Apr. 21, 2016

Related U.S. Application Data

(60) Provisional application No. 62/065,269, filed on Oct. 17, 2014.

(51) Int. Cl.
*A61F 2/06* (2013.01)
*A61F 2/95* (2013.01)
*A61F 2/966* (2013.01)
*A61F 2/97* (2013.01)

(52) U.S. Cl.
CPC ............. *A61F 2/966* (2013.01); *A61F 2/97* (2013.01)

(58) Field of Classification Search
CPC ...... A61F 2/84; A61F 2/95; A61F 2/97; A61F 2/966
See application file for complete search history.

(56) References Cited

U.S. PATENT DOCUMENTS

| 7,758,624 | B2 * | 7/2010 | Dorn | A61F 2/958 |
| | | | | 623/1.11 |
| 7,918,880 | B2 * | 4/2011 | Austin | A61F 2/95 |
| | | | | 623/1.11 |
| 2001/0056295 | A1 | 12/2001 | Solem | |
| 2002/0183826 | A1 | 12/2002 | Dorn et al. | |
| 2005/0165352 | A1 | 7/2005 | Henry et al. | |
| 2006/0184226 | A1 | 8/2006 | Austin | |
| 2008/0161902 | A1 | 7/2008 | Poulsen | |
| 2009/0319019 | A1 | 12/2009 | Parker | |

* cited by examiner

*Primary Examiner* — Victor Nguyen
(74) *Attorney, Agent, or Firm* — Brinks Gilson & Lione

(57) ABSTRACT

A medical instrument is provided including, an expandable tip which is embedded within a sheath. The expandable tip comprises a plurality of fingers which extend distally from the embedded portion. The plurality of fingers are heat set in a first position so that the distal ends of the fingers define a distal opening, where the distal opening has a smaller diameter than the embedded portion of the expandable tip. The plurality of fingers is reversibly expandable to a second position, creating a larger distal opening to deploy an expandable accessory.

19 Claims, 9 Drawing Sheets

EXPANDING SHEATH TIP

CROSS REFERENCE

The present application is a continuation application of, and claims all benefit pursuant to 35 U.S.C. § 119(e) of U.S. Provisional Application Ser. No. 62/065,269, "Expanding Sheath Tip", filed Oct. 17, 2014, which is incorporated by reference in its entirety.

BACKGROUND

The field of the present disclosure relates to catheters and sheaths to be used in intraluminal medical procedures.

Intraluminal procedures often involve delivery of an expandable device such a stent or plug to an area within a body passage. These expandable devices are frequently delivered within sheaths which are advanced over wire guides to the target area. However, delivery sheaths can have a relatively large diameter while intraluminal passages can be relatively narrow. Furthermore, wide sheaths advancing over narrow wire guides often have difficulty tracking on the wire guide as it curves through tortuous curvature.

What is needed is a delivery sheath with a small, tapered, distal tip which can track well on a wire guide through tortuous curvature and penetrate narrow portions of an intraluminal passage. The distal tip of this delivery sheath may then be expandable so that the expandable device therein may pass through the distal end of the sheath to be deployed. It is further desirable that once the device has been deployed, that the distal tip of the sheath return to its small tapered configuration to prevent complications during retraction of the delivery sheath.

SUMMARY

Further areas of applicability will become apparent from the description provided herein. It should be understood that the description and specific examples are intended for purposes of illustration only and are not intended to limit the scope of the present disclosure.

In one form of the present disclosure, a medical device is provided comprising a sheath and an expandable tip. The sheath comprises a wall which defines a lumen, and the expandable tip is coupled to the wall of the sheath. The expandable tip comprises a plurality of fingers which extend distally from the sheath. The plurality of fingers are heat set in a first position so that the distal ends of the plurality of fingers define a distal opening with a first diameter. This first diameter is less than the diameter of a proximal opening at the proximal end of the expandable tip. Additionally, the plurality of fingers is reversibly expandable to a second position wherein the distal opening has a larger second diameter.

In another form, a medical device is provided comprising a sheath, a catheter, and an expandable accessory. The sheath comprises a lumen and an expandable tip. The expandable tip has a plurality of fingers extending distally. The plurality of fingers are heat set in a first position so that the distal ends of the fingers define a distal opening. The distal opening has a diameter which is less than a diameter of the embedded portion. Further, the plurality of fingers is reversibly expandable to a second position having a larger diameter than the distal opening had in the first position. The catheter is positioned within the lumen of the sheath and comprises an enlarged portion projection outward from an outer surface of the catheter. The enlarged portion is arranged within the sheath to move an expandable accessory through the expandable tip.

BRIEF DESCRIPTION OF SEVERAL VIEWS OF THE DRAWINGS

The disclosure may be more fully understood by reading the following description in conjunction with the drawings, in which.

The drawings described herein are for illustration purposes only and are not intended to limit the scope of the present disclosure in any way.

DETAILED DESCRIPTION

Figure 1A:
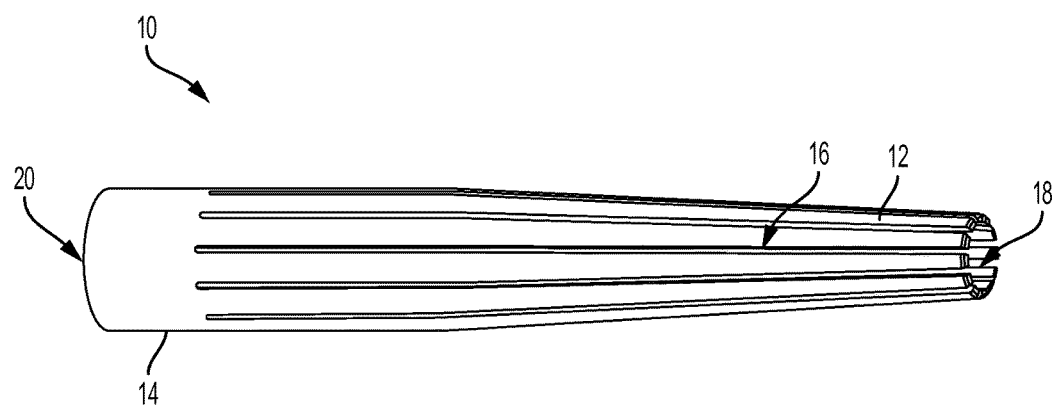
FIG. 1A is orthogonal view of an expandable tip in a first tapered position.
Figure 1B:
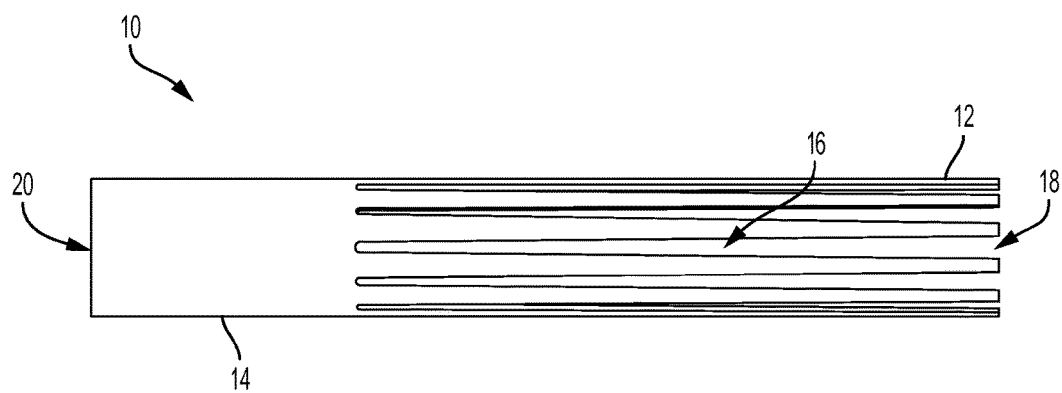
FIG. 1B is a side plan view of an expandable tip in an expanded second position.

Referring now to the drawings, and particularly to FIGS. 1A and 1B, an expandable tip 10 for a medical device is shown. The expandable tip 10 comprises a portion 14 which is designed to be coupled to a sheath 26, and a plurality of fingers 12 which extend distally from the coupled portion 14 and encompass at least one lumen 28. Together, the distal ends of the plurality of fingers 12 form a distal opening 18 on the expandable tip 10. As shown in FIG. 1A, the plurality of fingers 12 may be heat set in a tapered first position so that, when resting, the diameter of the distal opening 18 may be less than a proximal opening 20 on the proximal end of the expandable tip 10.

The plurality of fingers 12 of the expandable tip 10 are expandable to a second position, as shown in FIG. 1B. In this second position, the distal opening 18 of the expandable tip 10 has a diameter which may be larger than the diameter of the distal opening 18 in the first tapered position. Depending on the configuration and purpose of the device it may be desirable that, in the second position, the distal opening 18 has a diameter which may be equal to or greater than the diameter of the proximal opening 20 of the expandable tip 10. However, in other embodiments it may only be necessary for the expandable tip 10 to expand to a second position which has a greater diameter than in the first position, but smaller than the diameter of the proximal portion of the expandable tip 10 or than the diameter of the sheath 26.

The expandable tip 10 may be reversibly expandable, meaning that the fingers 12 may be expanded to the second position, but will return to the first position either by an external force or by their own internal forces. The fingers 12 may be returned to the first position by an additional sheath (not shown) which may be moved over the outside of the expandable tip, or by a covering 30 which encircles the plurality of finger 12, and which has a tendency to retract after being expanded. Alternatively, the fingers 12 may be made of a material, such as Nitinol or similar alloys, so that the fingers 12 may be heat set in the first position, and return to that first position after being expanded to the second position.

The expandable tip 10 provides rigidity to the distal end of the associated medical device. As a result, the expandable tip 10 may be made of a rigid material such as a metal alloy, like stainless steel or nitinol. The rigidity of the expandable tip 10 may increase the ability of the distal opening 18 formed by the fingers 12 to track on a wire guide 24 while the associated device is being advanced through an intraluminal passage 58.

The plurality of fingers 12 are arranged such that a gap 16 exists between each of the fingers 12. It may be desirable that when the expandable tip 10 is in the tapered first position, the gaps 16 have a substantially uniform width from the proximal end to the distal end of the fingers 12. In the second position, the gaps 16 between the fingers 12 have a width which increases from the proximal to distal end. For such a configuration, each of the fingers 12 may require a taper, in that the circumferential width of each finger 12 decreases from the proximal to distal end. Alternative configurations may be acceptable, however, wherein the fingers 12 are a uniform circumferential width from proximal to distal end, or wherein the width of the gaps 16 decrease or increase extending distally even while in the first position.

FIGS. 1A and 1B show an embodiment having twelve fingers 12, although other embodiments may have more or less. A larger number of fingers 12 may require thinner gaps 16 or thinner fingers 12, which may make the expandable tip 10 easier to expand from the first position to the second position. A fewer number of fingers 12 may require circumferentially wider fingers 12 or wider gaps 16, which may result in more structural rigidity to the expandable tip 10, at the expense of increased resistance to expansion. Furthermore, the circumferential width of the fingers 12 and the thickness of the fingers 12 may also be design considerations for the number of fingers 12. Fewer thin fingers 12 with a larger circumferential width may provide comparable rigidity to a large number of thick, circumferentially narrow fingers. It may also be desirable to vary the thickness of the fingers 12 as they extend distally to alter the difficulty of expansion in different portions of the expandable tip 10. Depending on at least these design considerations, it may be preferable to have between three and sixteen fingers 12.

Figure 2:
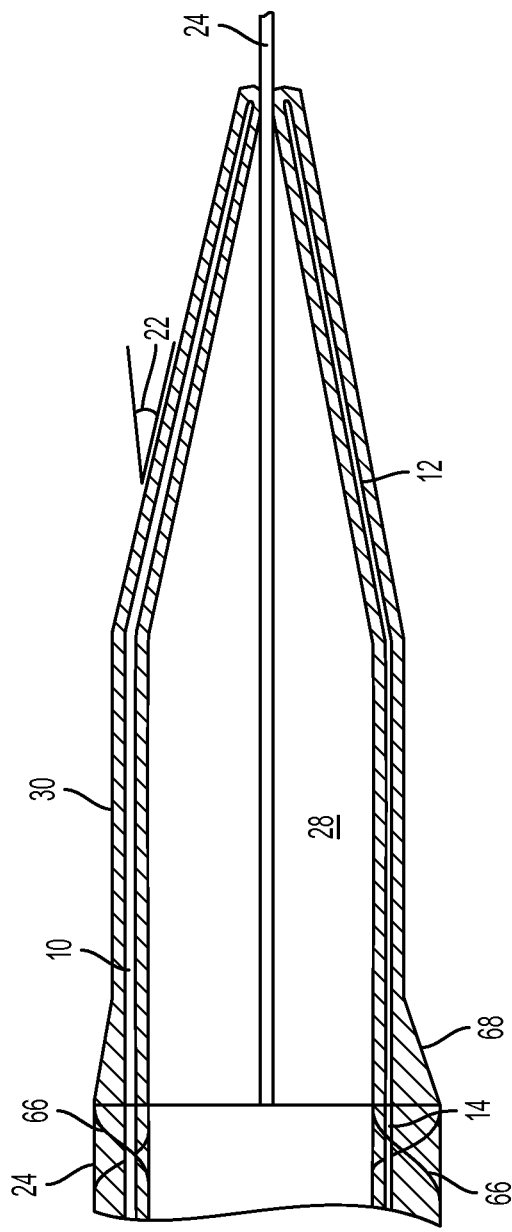
FIG. 2 is a cross-sectional view of a medical device comprising a sheath, an expandable tip, and a wire guide.

Referring to FIG. 2, a medical device is shown comprising an expandable tip 10 coupled to a sheath 26, and a wire guide 24 positioned in a lumen 28 of the sheath 26 and expandable tip 10. In this embodiment of the device, the expandable tip 10 comprises an embedded portion 14 which may be embedded within the walls 64 of the sheath 26. The portion of the expandable tip 10 which is not embedded within the sheath 26 may be embedded within an expandable covering 30. The plurality of fingers 12 shown in FIG. 2 form a distal end for the expandable tip 10 which may be substantially closed, only allowing a wire guide 24 through. The material of the expandable covering 30 may form a seal against the wire guide 24 passing through the distal opening 18 of the sheath 26.

The expandable tip 10 may be secured to the sheath 26 in several ways. The embedded portion 14 may comprise openings through or along its outer surface. These openings would be filled by the material of the walls 64 of the sheath 26, securing the expandable tip to the sheath 26. Alternatively, and as shown in the embodiment of FIG. 2, a wire 66 or a plurality of wires 66 may be embedded within the walls 64 of the sheath 26. These wires 66 may be welded to the embedded portion 14 of the expandable tip 10 to secure the expandable tip 10 to the sheath 26.

The expandable covering 30 shown in FIG. 2 comprises a continuous shell wherein a portion of the expandable tip 10 may be embedded within the walls of the shell. The material of the covering 30 may fill the gaps 16 between the fingers 12 of the expandable tip 10, so that, when the expandable tip 10 may be moved from the tapered first position to the second position, the covering 30 material between the gaps 16 of the fingers 12 stretches to accommodate the increased diameter of the distal opening 18 of the expandable tip 10. If the covering 30 is made of an elastic material such as nylon or silicone, the elastic resistance of this material within the gaps 16 of the expandable tip 10 may allow the expandable tip 10 to return to the tapered first position after being expanded to the second position. Alternatively, the expandable covering 30 may be designed to not be a continuous shell, but instead to encase each finger 12 individually. In such an embodiment, each portion of the covering 30 covering a finger 12 would be unconnected to each other portion of the covering 30.

It may be desirable that the proximal portion of the covering 30 which contacts the sheath 26 has a substantially similar diameter as the sheath 26, preventing edges which might cause the device to catch on an obstruction while advancing or retracting. To accomplish this, the covering 30 may have a thickness which matches the catheter 36 at least on the proximal portion of the covering 30. Distal from this portion, the covering 30 may have a tapering portion 68 in which the thickness of the covering 30 decreases distally. Alternatively, the covering 30 may have a constant thickness throughout the length of the expandable tip 10, although this may cause difficulty in maintaining a large distal opening 18 if the thickness and diameter of the wall 64 of the sheath 26 is too great To prevent cracking of the covering 30, the maximum expansion of the expandable tip 10 should be considered in the design of spacing of the gaps 16 and fingers 12. For example, if the elasticity and toughness of a covering 30 material is such that it may expand to twice or three times its resting size without deforming or breaking, then the gap 16 between fingers 12 should be such that from the first position to the second position, no portion of the gap 16 will stretch to a width of more than twice the original width in the first position. Similar design consequences exist for covering 30 materials capable of stretching more or less than the above example. Since the distal portions of the gap will likely stretch more than the proximal portions, it may be desirable to define an expansion limit in terms of the proximal and distal portions of the gaps 16. To accommodate a desired width for the gaps 16, the fingers 12 have a circumferential width which varies from the proximal to distal ends of the fingers. If the gaps 16 maintain a constant width while the expandable tip 10 is in the first position, then the fingers 12 will likely have a circumferential width which tapers as the fingers 12 extend distally. It may also be desirable for the thickness of the fingers 12 to decrease as the fingers 12 extend distally to give increased flexibility in the distal portions of the expandable tip 10.

The embodiment shown in FIG. 2 shows an expandable tip 10 with fingers 12 having a shallow taper angle 22 in the tapered first position, with respect to the axis of the device. A shallow taper angle 22 has the advantage of providing less resistance to expansion of the distal opening 18 from the first position to the second position. Further, a shallow taper angle 22 may provide less resistance if catheters 36 or wire guides 24 should be retracted proximally through the lumen 28 of the sheath 26. A wide range of taper angles 22, 32, 44, 46 may be acceptable under the design requirements and the components to be employed with the expandable tip 10, however, for a shallow taper angle 22, an angle equal to or less than 45 degrees may be ideal to minimize resistance to expansion. Alternatively, the taper of the fingers 12 could have a convex or concave curved shape instead of a linear angled taper.

Figure 3A:
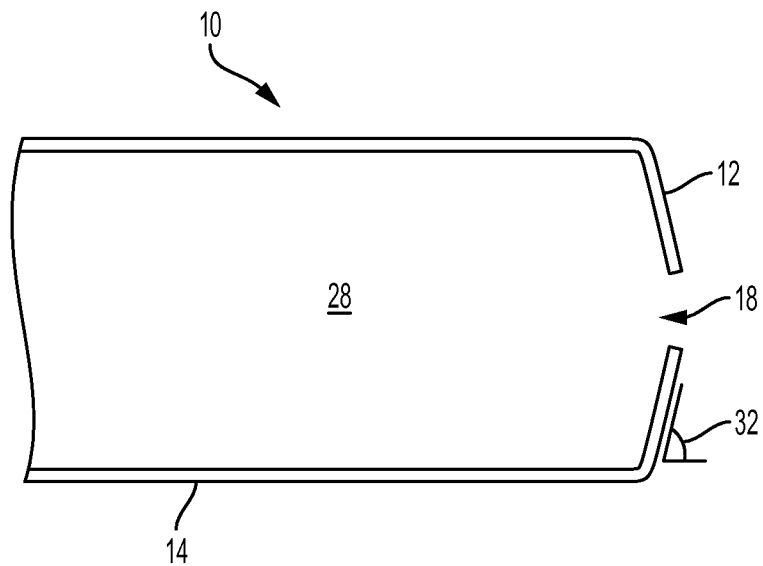
FIG. 3A is a cross-sectional view of an expandable tip in a first tapered position.
Figure 3B:
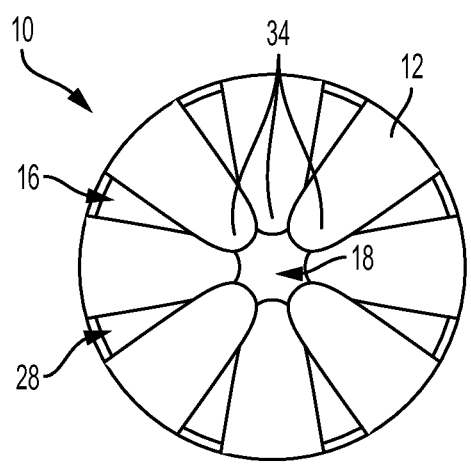
FIG. 3B is a front plan view of an expandable tip in a first tapered position.

Referring to FIGS. 3A and 3B, another embodiment of the expandable tip 10 is shown having fingers 12 which taper to the distal opening 18 at a steep taper angle 32. With a shallow taper angle 22, a covering 30 may be needed around the fingers 12 to prevent one or more fingers 12 from catching on obstructions within the intraluminal passage 58. However, a steep taper angle 32 of 60 degrees or greater has the advantage of minimizing this risk, as the associated fingers 12 are shorter, closer to the distal end of the sheath 26, and may be wider, providing additional rigidity. In such an embodiment, a covering 30 may not be needed. Another advantage may be that a steep taper angle 32 provides greater accuracy in placing an expandable accessory 38, such as a stent or plug, in difficult passages, such as in a sharp bifurcation of the intraluminal passage 58.

The medical device may be advanced through an intraluminal passage 58 over a wire guide 24. While the medical device is being advanced, it is desirable that the expandable tip 10 tracks well with the wire guide 24, flexing through curves within the intraluminal passage 58 and keeping the wire guide 24 within the distal opening 18 of the expandable tip 10. If the wire guide 24 is forced into one of the gaps 16 between the fingers 12, the medical device may seize on the wire guide 24 and be unable to advance further. Where the fingers 12 have a shallow taper angle 22, a covering 30 may be used to ensure that the wire guide 24 may be maintained within the distal opening 18. However, if a covering 30 is not used, as shown in FIGS. 3A and 3B, then an arrangement of fingers 12 with steep taper angles 32 and overlapping distal ends 34 may be used to define the distal opening 18 and prevent the wire guide 24 from exiting the distal opening 18 and entering a gap 16 between the fingers 12. The embodiment shown in FIG. 3B comprises eight fingers 18 with rounded distal ends 34. At least a portion of each finger 12 overlaps with a portion of each adjacent finger 12. The arrangement shown has four fingers 12 on an upper layer overlapping with four fingers 12 on a lower layer, however, the number of fingers 12 and the overlapping pattern of their distal ends 34 may be subject to design requirements and may be varied so that the expandable tip 10 has more or fewer fingers 12, preferably between three and sixteen fingers 12. Ideally, each finger 12 will overlap with a portion of at least one of its adjacent fingers 12. Alternatively, an additional structure may be included, such as a plurality of struts, which are coupled to the fingers 12 in the first position, which may assist in helping the fingers 12 stay in the first position and track over the wire guide 24. Such struts may be built into an expandable accessory 38 or a catheter 36 so that when the expandable accessory 38 or catheter 36 is moved through the expandable tip 10, the struts detach and allow the fingers 12 to expand to the second position.

Figure 4:
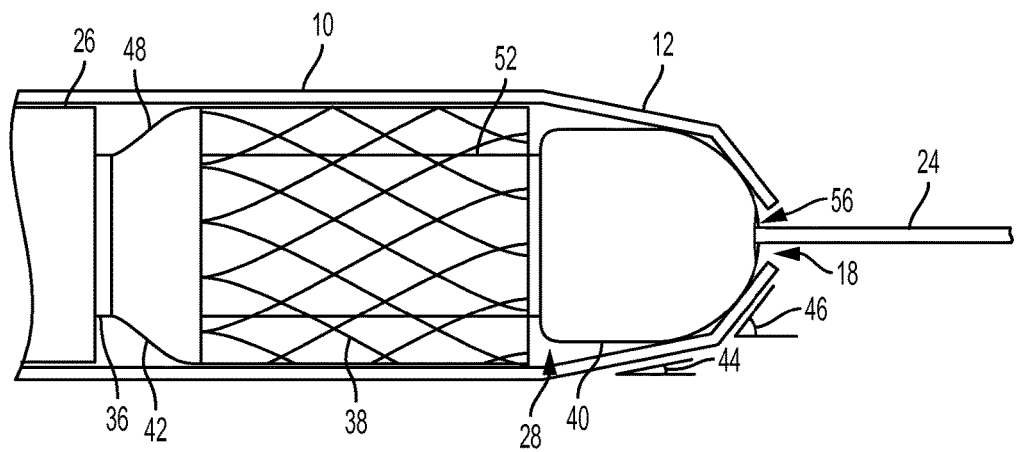
FIG. 4 is a partial cross-sectional view of a medical device comprising a sheath, a catheter, an expandable tip, and an expandable accessory.

Referring to FIG. 4, another embodiment of a medical device is shown comprising a sheath 26 and an expandable tip 10 having a plurality of fingers 12 with two stages of tapering distally toward a distal opening 18. In the proximal first stage of each finger 12, each finger 12 has a shallow taper angle 44 which allows easy initial expansion of the fingers 12 as the catheter 36 and expandable accessory 38 are moved through the lumen 28 of sheath 26 against the fingers 12 of the expandable tip 10. A second stage of each finger 12, extending distally from the first stage, comprises a steeper taper angle 46. The combination of angles 44, 46 may allow the plurality of fingers 12 to gain some of the advantages of both the single stage shallow taper angle 22 embodiment shown in FIG. 2 and the single stage steep taper angle 32 embodiment shown in FIGS. 3A and 3B. The second stage with a steep taper angle 46 prevents the fingers 12 from catching on obstructions as it is advanced through an intraluminal passage. As a result, a covering 30 over the expandable tip 10 may not be needed for such an embodiment. Typical shallow taper angles 44 will be less than 45 degrees, while typical steeper angles 46 will be equal to or greater than 45 degrees.

Alternatively, the embodiment may fingers 12 each having a plurality of stages with a plurality of different angles. It may be desirable that in such a configuration, each stage has a taper angle 22, 32, 44, 46 which may be less than any relatively distal stage, while each stage has a taper angle 22, 32, 44, 46 which may be greater than any relatively proximal stage. The most proximal stage may have a very shallow taper angle 22, 32, 44, 46 which may be greater than 0 degrees, while the most distal stage may have a very steep taper angle 22, 32, 44, 46 which may be less than 90 degrees. Typically, the overall taper angle 22, 32, 44, 46 of the fingers 12 for such configurations may be between 10 and 80 degrees.

The expandable tip 10 shown in FIG. 4 may be coupled to the outer surface of the sheath 26 rather than being fully embedded within the wall 64 of the sheath 26. This may be desirable for ease of manufacture. The inner surface of the expandable tip 10 may be coupled to the outer surface of the sheath 26 in a variety of ways, including an applied epoxy, one or more ridges projecting inward from the inner surface of the expandable tip 10 into the outer surface of the sheath 26, or openings within the inner surface of the expandable tip 10, which projections extending outward from the sheath's 26 outer surface are slotted into. In a similar alternative, the outer surface of the expandable tip 10 may be coupled to the inner surface of the sheath 26, wherein at least a portion of the expandable tip 10 extends into the lumen 28 of the sheath 26.

Additionally, the embodiment shown in FIG. 4 includes a catheter 36 arranged within the lumen 28 of the sheath 26 and an expandable accessory 38 arranged on the distal portion of the catheter 36. The expandable accessory 38 shown may be a self-expanding stent, however, a variety of other expandable accessories 38 may be used instead including aspiration funnels and vascular plugs. The catheter 36 may further comprise additional control mechanisms to allow expansion of the expandable accessory 38 even when it is not self-expanding. The catheter 36 may also include a rounded distal tip 40, which prevents damage to the intraluminal passage 58 and assists in expanding the distal opening 18 of the expandable tip 10. To assist with the expansion of the fingers 12 further, it may be desirable that the distal tip 40 of the catheter 36 be larger in diameter than the cross-sectional area of the lumen 28 of the catheter 36 which may be configured to receive the expandable accessory 38.

The distal tip 40 of the catheter may be positioned as close as possible to the fingers 12 of the expandable tip 10 while the sheath 26 is being advanced within the intraluminal passage 58. If the distal tip 40 of the catheter 36 is in proximity to the fingers 12, then the opening of the inner lumen 56 of the catheter 36 will be as close as possible to the distal opening 18. It may be desirable to have the opening of the inner lumen 56 positioned closely to the distal opening 18 to provide support to a wire guide 24 which may pass through the inner lumen 56. In the configuration shown in FIG. 4, the inner lumen 56 supports the wire guide 24 and assists the wire guide 24 in tracking on the fingers 12 even while in tortuous passages. It may be desirable to configure the distal tip 40 of the catheter 36 which a curved distal face which contacts the fingers 12, as shown in FIG. 4, to bring the opening of the inner lumen 56 and the distal opening 18 into closer proximity. This may also be accomplished by configuring the front face of the distal tip 40 to match the inner shape and angle of the fingers 12 and covering 30 while in the first position.

The self-expanding accessory 38 shown in FIG. 4 may be disposed between the outer surface 52 of the catheter 36 and the walls 64 of the sheath 26 or expandable tip 10. The accessory's 38 position within the sheath 26 may be controlled in part by an enlarged portion 42 arranged on the outer surface 52 of the catheter 36, proximally from where the expandable accessory 38 is positioned. The enlarged portion 42 comprises a collar which extends radially from the outer surface 52 of the catheter 36. The outer surface of the enlarged portion 42 may contact or may be in the vicinity to the walls 64 of the sheath 26. The catheter 36 may be advanced to push the expandable accessory 38 towards the distal opening 18. Motion of the enlarged portion 42 of the catheter 36 across the expandable tip 10 moves the plurality of fingers 12 between the first position and the second position. Alternatively, the sheath 26 and expandable tip 10 may be retracted, with the catheter 36 securing the expandable accessory 38 in place so that it expands as the distal opening 18 of the expandable tip 10 passes around it.

Figure 5A:
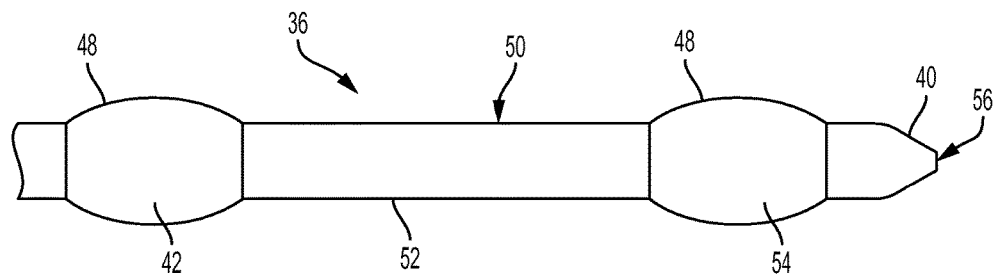
FIGS. 5A-5C are side plan views of different embodiments of a catheter configured to receive an expandable accessory.

Referring to FIG. 5A, an embodiment of the catheter 36 is shown comprising a proximal enlarged portion 42 and a distal enlarged portion 54 arranged on the outer surface 52 of the catheter 36. The distal tip 40 of the catheter 36, also includes an opening 18 into a lumen 28 through which a wire guide 24 may pass through.

The proximal and distal enlarged portions 42, 54 are positioned to create a region on the catheter 36 which may be configured to receive the expandable accessory 38 in its compressed position. The enlarged portions 42, 54 then can control the movement of the expandable accessory 38 with respect to the sheath 26 and expandable tip 10. The proximal enlarged portion 42 may be used to advance the accessory 38 or to prevent retraction of the accessory 38 while the sheath 26 and expandable tip 10 are being retracted. Similarly, the distal enlarged portion 54 may be used to retract the accessory 38 or to prevent premature deployment of the accessory 38 if the sheath 26 and expandable tip 10 are advanced over the catheter 36.

After deploying the expandable accessory 38, it may be desirable to advance the sheath 26 over the catheter 36 so the entire device may be retracted as a single member. To accommodate this, it may be necessary to include inclines 48 on the proximal sides of the enlarged portions 42, 54 which allow the fingers 12 of the expandable tip 10 to easily expand as it advances over the enlarged portions 42, 54 through the distal opening 18 of the expandable tip 10. The taper angle 22, 32, 46 at the distal end of the fingers 12 determines how steep the incline 48 on the enlarged portion 42, 54 should be. A shallow taper angle 22 on the fingers 12, such as those equal or less than 45 degrees, can expand to accommodate a steeper incline 48 on the proximal end of an enlarged portion 42, 54. However, some steep incline 48 angles, such as incline 48 angles of greater than 45 degrees, may still be too steep to allow for easy expansion of the fingers 12. Similarly, a steep taper angle 32, 46 on the distal end of the fingers 12, such as those greater than 60 degrees, require that the incline 48 be more gradual than it would be to accommodate a shallow taper angle 22, possibly as low as a 5 degree incline 48 angle. It may only be necessary that the inclines 48 are positioned on the proximal side of the enlarged portions 42, 54, however for ease of manufacturing, it may be desirable to include inclines 48 on both the proximal and distal sides of the enlarged portions 42, 54. However, an incline 48 on the distal side of the proximal enlarged portion 42 may cause the expandable accessory 38 to become wedged between the proximal enlarged portion 42 and the sheath 26 as the sheath 26 is retracted from the catheter 36.

Figure 5B:
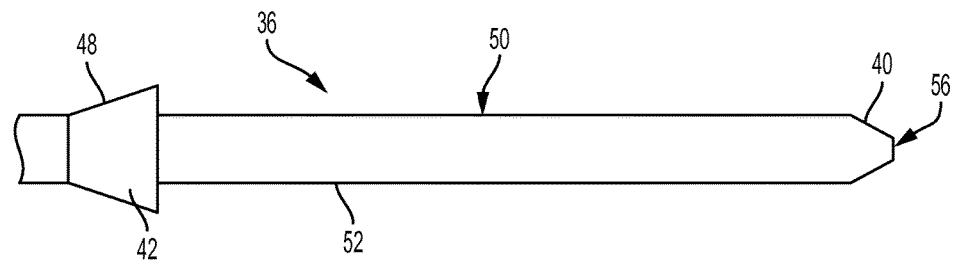

Referring to FIG. 5B, an alternative embodiment of the catheter 36 is shown. In this embodiment, the catheter 36 comprises only one enlarged portion 42 on the proximal end of the space 50 configured to receive an expandable accessory 38. Further, the enlarged portion 42 comprises an incline 48 only on the proximal side of the enlarged portion 42, whereas the distal side of the enlarged portion 42 may be substantially vertical. The vertical distal side allows the enlarged portion 42 to more effectively exert force to move the expandable accessory 38 and prevents the accessory 38 from moving over the enlarged portion 42 and becoming wedged between the enlarged portion 42 and the sheath 26 as the catheter 36 is advanced.

Figure 5C:
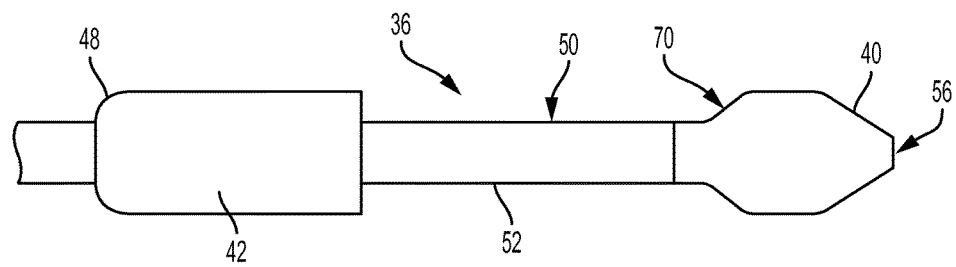

Referring to FIG. 5C, an alternative embodiment of the catheter 36 is shown. In this embodiment, the catheter 36 comprises an elongated proximal enlarged portion 42 and an enlarged distal tip 40. The proximal elongated enlarged portion 42 has a substantially vertical distal side, and a rounded incline 48 on the proximal side. The rounded incline 48 may be difficult for some steep taper angle configurations of the expandable tip 10 advance over. However, when the catheter 36 is advanced through the expandable tip 10, a portion of the elongated enlarged portion 42 may remain within the distal opening 18 of the expandable tip 10. The longer the enlarged portion 42, the easier it may be for an operator to maintain the catheter 36 in this position while deploying the expandable accessory 38. Once the accessory 38 is deployed, the catheter 36 may be at least partially retracted without further expansion over the enlarged portion 42.

Additionally, after deployment of the expandable accessory 38, it may not be necessary to retract the entire catheter 36 into the lumen 28 of the sheath 26. However, it may be important that no edges be exposed outside the sheath 26 during retraction which might catch on an obstruction. To prevent this, the enlarged distal tip 40 shown in FIG. 5C may also comprise a catch 70 on the proximal side of the distal tip 40. This catch 70 may be a rise in the diameter of the catheter 36 which may be substantially vertical, curved, or angled. When the catheter 36 is retracted into the sheath 26, the catch 70 will rest against the distal end of the expandable tip 10. To prevent any edges from forming on this connection, the size of the catch 70 may be less than or equal to the thickness of the distal end of the fingers 12 or the fingers 12 and covering 30, so that the catch 70 rests flush against the distal end of the expandable tip 10. This configuration may be particularly desirable to use alongside embodiments of the expandable tip 10 having steep taper angles 32, 46.

Figure 6A:
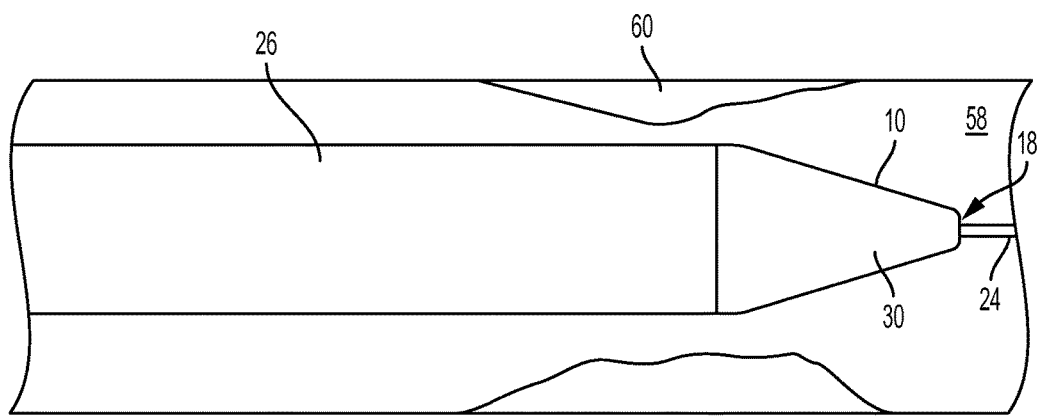
FIGS. 6A-6C are partial cross-sectional views of an intraluminal passage showing a medical device, a wire guide, a catheter, and an expandable accessory.
Figure 6B:
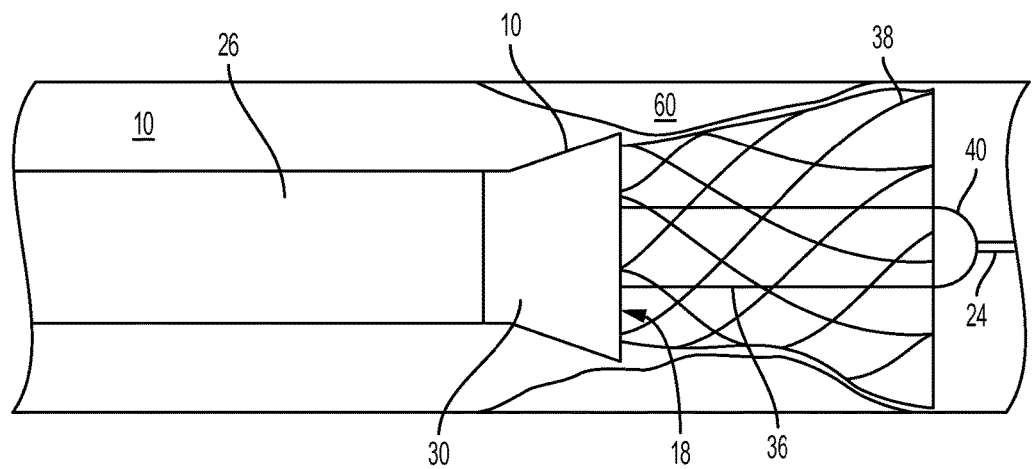
Figure 6C:
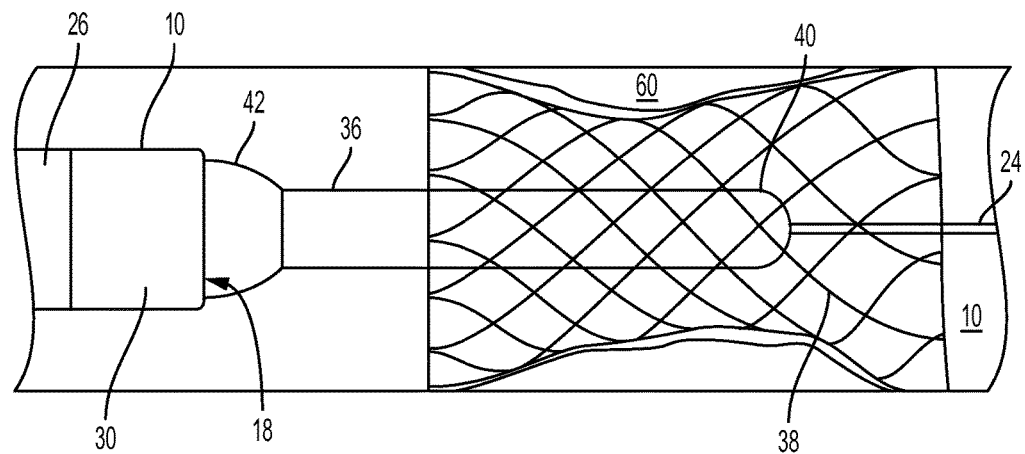

Referring to FIGS. 6A-6C, the method of operation is shown for the medical device described above. The example shown in these figures demonstrates deploying a self-expanding stent, but the procedure would be similar or identical for a variety of expandable accessories 38 designed to be deployed by the device.

Referring to FIG. 6A, an intraluminal passage 58 is shown having a target area 60. The expandable accessory 38 may be positioned within the sheath 26 proximal from any tapered portion of the expandable tip 10. The medical device may be advanced over a wire guide 24 until the distal end of the expandable accessory 38 has passed the distal end of the target. Radiopaque markers may be positioned on the distal end of the expandable accessory 26 or the proximal end of the expandable tip 10 to assist in positioning of the expandable accessory 38 within the intraluminal passage 58. In the configuration shown in FIG. 6A, the expandable tip 10 may be in a tapered first position to ease advancement of the sheath 26 through the intraluminal passage 58 and into the target area 60.

Referring to FIG. 6B, the medical device is shown as the sheath 26 is being retracted. The catheter 36 within the sheath 26 may remain unmoved so that the expandable accessory 38 begins to advance through the distal opening 18 of the expandable tip 10. In some embodiments, the catheter 36 may also be advanced to assist in deployment of the expandable accessory 38, however, this may require additional considerations in initial placement of the medical device within the intraluminal passage 58. Once the distal opening 18 is proximal to a portion of the expandable accessory 38, the accessory 38 will begin to expand to fill the intraluminal passage 58. During this process the expandable tip 10 will expand to a second position, stretching the covering 30.

Referring to FIG. 6C, the expandable accessory 38 is shown fully deployed within the intraluminal passage 58 covering the target area 60. The sheath 26 may now be advance over the catheter 36 so that the sheath 26 and catheter 36 may be retracted together. Alternatively, the catheter 36 may now be retracted into the sheath 26, or the sheath 26 and catheter 36 may be retracted together without recapturing the distal end 40 of the catheter 36 within the sheath 26. To accomplish this, the expandable tip 10 may have to expand the distal opening 18 again to accommodate the enlarged portion 42 of the catheter 36. If the catheter 36 includes a distal enlarged portion 54 as shown in FIG. 5A, an incline 48 arranged on the proximal side of the distal enlarged portion 54 may allow for easier recapture of the distal end 40 of the catheter 36. Once the catheter 36 has been retracted into the sheath 26, the expandable tip 10 will return to its first position so that the distal opening 18 will return to its original diameter. This closure assists in keeping the catheter 36 within the sheath 26 during retraction.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:

1. A medical device, comprising:
a sheath comprising a wall which defines a lumen; and
an expandable tip coupled to the wall of the sheath at a proximal end of the expandable tip, wherein the expandable tip comprises a plurality of fingers extending distally from the proximal end, each of the plurality of fingers having a distal end, wherein the plurality of fingers are heat set in a first position so that the distal ends of the plurality of fingers define a distal opening with a first diameter which is less than a diameter of a proximal opening at the proximal end of the expandable tip, and wherein the plurality of fingers is reversibly expandable to a second position wherein the distal opening has a larger second diameter.

2. The medical device of claim 1, wherein the plurality of fingers has a taper angle less than 45 degrees.

3. The medical device of claim 1, wherein the plurality of fingers has a taper angle which is greater than 60 degrees.

4. The medical device of claim 1, wherein each of the plurality of fingers have a first proximal portion and a second distal portion, wherein a proximal taper angle on the proximal portion is less than a distal taper angle on the distal portion.

5. The medical device of claim 1, wherein the plurality of fingers are embedded within an expandable covering.

6. The medical device of claim 5, further comprising a gap between each of the plurality of fingers wherein the covering fills at least a portion of each of the gaps.

7. The medical device of claim 6, wherein when the fingers are in the first position, each of the gaps have a width which is substantially uniform from a proximal end to a distal end.

8. The medical device of claim 6, wherein when the fingers are in the second position, each gap has a distal portion and a proximal portion, wherein a distal width of the distal portion is at least two times a proximal width of the proximal portion.

9. The medical device of claim 1, wherein each of the plurality of fingers has a circumferential width which tapers distally.

10. The medical device of claim 1, wherein the plurality of fingers are configured to move from the first position by proximal motion of a catheter through the distal opening.

11. The medical device of claim 1, wherein each of the distal ends of the plurality of fingers, when the plurality of fingers are in the first position, overlaps with at least one other distal end of one of an adjacent finger.

12. The medical device of claim 1, wherein at least a portion of the expandable tip is embedded within the wall of the sheath.

13. The medical device of claim 1, wherein at least a portion of the expandable tip is coupled to an outer surface of the sheath.

14. The medical device of claim 1, wherein, when the expandable tip is in the second position, the diameter of the distal opening is larger than or equal to the diameter of the proximal end.

15. A medical device, comprising:
a sheath comprising a wall which defines a lumen; and
an expandable tip located at a distal end of the sheath, wherein the expandable tip comprises a plurality of fingers extending distally from a proximal end, each of the plurality of fingers having a distal end, wherein the plurality of fingers are heat set in a first position such that the expandable tip tapers distally to a distal opening having a first diameter which is less than a diameter of a proximal opening at the proximal end of the expandable tip, wherein the plurality of fingers is reversibly expandable to a second position wherein the distal opening has a larger second diameter, and wherein the plurality of fingers are embedded within an expandable covering.

16. The medical device of claim 15, further comprising a catheter positioned within the lumen of the sheath, wherein the catheter has an enlarged portion projecting from an outer surface of the catheter, and wherein the enlarged portion is arranged within the sheath to move an expandable accessory through the expandable tip.

17. The medical device of claim 16, wherein the catheter comprises a proximal enlarged portion and a distal enlarged portion on the outer surface of the catheter, and wherein the catheter is arranged to receive the expandable accessory between the proximal and distal enlarged portions.

18. The medical device of claim 16, wherein the enlarged portion of the catheter comprises a proximal portion with an incline from the outer surface extending distally and projecting outwardly from the outer surface.

19. The medical device of claim 18, wherein the enlarged portion further comprises a distal portion with an incline from the outer surface extending proximally and projecting outwardly from the outer surface.

\* \* \* \* \*